United States Patent [19]

Sowerby et al.

[11] Patent Number: 4,817,021

[45] Date of Patent: Mar. 28, 1989

[54] MOISTURE AND DENSITY DETERMINATION

[75] Inventors: Brian D. Sowerby; Nicholas G. Cutmore, both of New South Wales, Australia

[73] Assignee: Commonwealth Scientific and Industrial Research Organisation, Campbell, Australia

[21] Appl. No.: 821,491

[22] Filed: Jan. 22, 1986

[30] Foreign Application Priority Data

Jan. 24, 1985 [AU] Australia ............................ PG9011
Jul. 5, 1985 [AU] Australia ............................ PH1342
Aug. 8, 1985 [AU] Australia ............................ PH1852

[51] Int. Cl.$^4$ .................. G01N 27/22; G01N 23/203; G01B 15/02
[52] U.S. Cl. ................... 364/558; 250/359.1; 324/61 QS; 324/61 QL; 324/65 R; 364/563; 378/54
[58] Field of Search .................. 364/558, 563; 378/53, 378/54, 89; 250/359.1; 324/61 QS, 61 QL, 384, 65 R; 73/73, 304 C

[56] References Cited

U.S. PATENT DOCUMENTS

| | | | |
|---|---|---|---|
| 3,255,975 | 6/1966 | Malin et al. | 250/359.1 |
| 3,668,401 | 6/1972 | Shah et al. | 378/54 |
| 3,671,857 | 6/1972 | Bergmanis et al. | 324/61 QS |
| 3,746,975 | 7/1973 | Maltby | 73/304 C |
| 3,777,258 | 12/1973 | Wochnowski | 324/61.25 |
| 3,793,585 | 2/1974 | Wilska | 324/61 QS |
| 3,795,802 | 3/1974 | Powell | 250/384 |
| 3,811,087 | 5/1974 | Schmelzer | 324/61 P |
| 4,047,029 | 9/1977 | Allport | 364/563 |
| 4,114,090 | 9/1978 | Poskitt | 324/61 QS |
| 4,168,431 | 9/1979 | Henriksen | 378/53 |
| 4,266,425 | 5/1981 | Allport | 378/54 |
| 4,272,718 | 6/1981 | Kashiuchi et al. | 324/61 QL |
| 4,359,638 | 11/1982 | Allport | 378/54 |
| 4,362,939 | 12/1982 | Horiuchi et al. | 250/359.1 |
| 4,538,453 | 9/1985 | Simmons | 73/73 |
| 4,560,923 | 12/1985 | Hanson | 324/61 QL |
| 4,574,387 | 3/1986 | Gignoux et al. | 364/563 |
| 4,618,939 | 10/1986 | Davis | 364/558 |
| 4,683,904 | 8/1987 | Iltis | 324/61 QL |

FOREIGN PATENT DOCUMENTS

| | | |
|---|---|---|
| 2919230 | 11/1980 | Fed. Rep. of Germany ... 324/61 QS |
| 731133 | of 0000 | United Kingdom . |
| 675731 | of 0000 | United Kingdom . |
| 867143 | of 0000 | United Kingdom . |

*Primary Examiner*—Felix D. Gruber
*Attorney, Agent, or Firm*—Ladas & Parry

[57] ABSTRACT

Apparatus and methods for producing a signal or signals related to the moisture content of a substance using impedance, radio frequency loss or dielectric loss techniques are disclosed. Apparatus and methods for producing a signal or signals related to the density and/or thickness of a substance using backscattered gamma-rays are described. Apparatus and methods using a combination of a.c. impedance, radio frequency or dielectric loss and backscattered gamma-ray techniques for producing signals related to the moisture content, density and/or thickness of a substance are also described. Means and methods for determining the moisture content, density and/or thickness of the substance from the signal or signals are disclosed. The apparatus and methods are particularly applicable to determining the moisture content, density and/or thickness of coal and coke.

15 Claims, 4 Drawing Sheets

MOISTURE AND DENSITY DETERMINATION

This invention relates to apparatus and methods for producing a signal or signals related to the moisture content, density and/or thickness of a substance. The invention also includes apparatus and methods for determining the moisture content, density and/or thickness of the substance from the signal or signals. In this specification a reference to coal is also a reference to coke.

Measurements of the moisture content and/or density of a substance are required in a range of industrial processes. For example, they can be required during various stages of production to ensure uniform product quality.

In some applications it is also desirable to determine the moisture content and density of a substance on-line. This is particularly so when it is difficult to obtain a representative sample of a substance and also when measures of the moisture content and density of a substance are required quickly.

An accurate knowledge of the moisture contents of substances is often required in many aspects of production and utilisation to ensure a uniform product and/or batch.

Specifically for coal and coke:
(a) there is interest in measuring and controlling the moisture content of coking and steaming coals. Moisture in these coals has tended to increase largely because of the increased proportion of fine coal in preparation plants due to modern mining methods and to greater emphasis on fine coal recovery for economic reasons. Lower product coal moisture results in transport cost benefits, energy savings when the coal is consumed and reduced handling difficulties;
(b) in a coal washery, the on-line measurement of moisture in fine (minus 0.5 mm) product coal from disc and drum vacuum filters in coal preparation plants can be used to assist in developing control procedures for these units. Conventional methods of sampling and oven drying are two slow for plant control;
(c) when combined with an on-line ash measurement an on-line moisture measurement can be used to determine the specific energy of coal to be burned in a power station. Continuous determination of the specific energy of steaming coal permits better control of coal fired power stations.

In previous investigations of the measurement of moisture in coal by capacitance techniques as described in Green, R. M., Humidity and Moisture, A. Wexler (Ed.) Reinhold Publ. Corp., Vol. 4, p141, Hall D. A., Morris G. F. and Scott, C., Mining and Minerals Engineering, 1969 (November) p30 and Brown D. R., "Nuclear Assay of Coal (Vol. 5), Coal Btu Measurement Study—Monitoring Moisture in Coal", 1979 EPRI FP-989 Vol. 5, a ski arrangement has been used, in which a sensor rides of the surface of the coal sample under test. In one arrangement described in Green, R. M., Humidity and Moisture, A. Wexler (Ed.), Reinhold Publ. Corp., Vol. 4, 141 and in Hall, D. A., Morris, G. F. and Scott, C., Mining and Minerals Engineering, 1969 (November), 30 a keel plate penetrates the coal and the capacitance of a fringing electric field between the keel plate and surface ski is measured. A similar design in which two keel plates penetrate the coal sample, and the capcitance of a fringing electric field between the keel plates is measured, has also been used by Brown, D. R., "Nuclear Assay of Coal (Vol. 5), Coal Btu Measurement Study—Monitoring of Moisture in Coal", 1979, EPRI FP-989 Vol. 5.

In these investigations, keel plates are an essential component of the ski sensor in increasing the volume of the sample interrogated by the fringing electric field of the sensor. However a significant disadvantage of this design is the requirement for the sensor to penetrate a moving stream of coal on a conveyor belt, since this necessitates that the sensor be very rugged as indicated by Hall, D. A., Morris, G. F. and Scott, C., Mining and Minerals Engineering, 1969 (November), p30, and further, is an arrangemenet that may lead to a blockage (or damage) of the conveyor belt itself. A non-contacting measurement technique overcomes many of these problems but previous investigations by Brown, D. R., "Nuclear Assay of Coal (Vol. 5), Coal Btu Measurement Study—Monitoring of Moisture in Coal", 1979, EPRI FP-989 Vol. 5, have been unable to design a non-contacting sensor with an acceptable sensitivity to moisture in coal.

Measurement of the moisture content of a substance by a capacitance technique (a.c. impedance, radio frequency loss or dielectric loss) relies upon an increase in the dielectric constant of the substance, in proportion to moisture content, which influences the magnitude of the measured electrical quantity (for example, a.c. impedance). An increase in the measured dielectric constant of a substance with increased moisture content occurs because the dielectric constant of water is $\sim 80$, whereas many dry substances have a dielectric constant $\sim 10$ (see Handbook of Chemistry and Physics, R. C. Weast (Ed.), CRC Press Inc., (USA), 58th Edition, 1977–78).

In practice, the density and thickness of a substance will also influence the measurement of moisture content when using a capacitance technique, since it is the average dielectric constant of the volume interrogated by the capacitance sensor that influences the measured electrical quantity, and this will depend upon the amount (density and thickness) of a substance within the measurement volume.

It has been found that the measured count rate of Compton scattered gamma-rays measured by a gamma-ray backscatter gauge provides a measure of density of coal whose sample thicknesses are greater than about 120 mm. Disadvantageously, however, for coal samples having thicknesses less than 120 mm, it has been found that the Compton backscatter count rate is dependent on both the density and thickness of the sample and therefore the density of such coal samples cannot be reliably determined.

The measurement may also be influenced by the presence of dissolved salts in the water, but this influence typically increases with increasing measurement frequency, and for this reason most capacitance techniques (for moisture measurement) operate at radio frequencies (1–100 MHz).

An object of this invention is to provide an apparatus and method for producing a signal or signals related to the moisture content of a substance and from which the moisture content of the substance can be determined.

Another object is to provide an apparatus and method for producing signals related to the moisture content, density and/or thickness of a substance from which the moisture content density and/or thickness of the substance can be determined.

A further object is to provide an apparatus and method for producing a signal or signals related to the density and/or thickness of a substance from which the density and/or thickness of the substance can be determined.

Accordingly in a first embodiment this invention provides an apparatus for producing a signal or signals related to the moisture content of a substance from which the moisture content of the substance can be determined, the apparatus including:
(a) an a.c. signal generator connected across two electrodes located remote from the substance whereby an a.c. field generated therebetween passes through the substance; and
(b) measuring means associated with the generator for receiving an a.c. sample signal or signals related to the field passing through the substance for measuring a.c. impedance, radio frequency loss or dielectric loss of the substance and for deriving a moisture output signal or signals therefrom relates to the moisture content of the substance.

In one preferred form of the first embodiment the moisture output signal or signals are fed to a display or displays.

In a particularly preferred form of the first embodiment the apparatus also includes calculating means associated with the measuring means for calculating the moisture content of the substance from the moisture output signal or signals and preferably the moisture content of the substance is calculated in accordance with the algorithm $$\text{Moisture} = a_0 + a_1 C + a_2 G \quad (1)$$

where $a_0$, $a_1$ and $a_2$ are constants, C is susceptance and G is conductance.

In a second embodiment this invention provides an apparatus for producing signals related to the moisture content, density and/or thickness of a substance from which the moisture content, density and/or thickness of the substance can be determined, the apparatus including the apparatus of the first embodiment and:
(c) a gamma-ray source and a detector which are located remote from the substance wherein gamma-rays from the source irradiate the substance and the intensities of backscattered gamma-rays are measured by the detector; and
(d) processing means associated with the detector for deriving a density and/or thickness output signal or signals from the measured intensities which is/are related to the density and/or thickness of the substance.

In one preferred form of the second embodiment both the moisture output signal or signals and the density and/or thickness output signal or signals are fed to a display or displays.

In a particularly preferred form of the second embodiment the apparatus also includes calculating means associated with the measuring means and processing means for calculating the moisture content, density and/or thickness of the substance from the moisture and the density and/or thickness output signal or signals.

Preferably the moisture content of the substance is calculated in accordance with the algorithm $$\text{Moisture} = a_0 + a_1 C + a_2 G + a_3 \rho \quad (2)$$

where $a_0$, $a_1$, $a_2$ and $a_3$ are constants, C is susceptance, G is conductance and $\rho$ is density of the substance.

Optionally the density ($\rho$) of said substance is calculated in accordance with the algorithm $$\rho = b_0 + b_1 C1 + b_2 (C2/C3) \quad (3)$$

where $b_0$, $b_1$ and $b_2$ are constants and C1, C2 and C3 are the measured Compton scatter count rates for preselected gamma-ray energies or energy ranges, and wherein the moisture content of said substance is calculated in accordance with the algorithm $$\text{Moisture} = d_0 + d_1 C + d_2 G + d_3 \rho \quad (4)$$

where $d_0$, $d_1$, $d_2$ and $d_3$ are constants, C is susceptance and G is conductance.

In a third embodiment this invention provides an apparatus for producing a signal or signals related to the density and/or thickness of the substance from which the density and/or thickness of the substance can be determined, the apparatus including:
(a) a gamma-ray source and a detector which are located remote from the substance wherein gamma-rays from the source irradiate the substance and the intensities of backscattered gamma-rays are measured by the detector; and
(b) processing means associated with the detector for deriving a density and/or thickness output signal or signals from the measured intensities related to the density of the substance.

In a preferred form of the third embodiment the density and/or thickness output signal or signals are fed to a display.

In a particularly preferred form of the third embodiment the apparatus also includes calculating means associated with the output of the processing means for calculating the density and/or thickness of the substance from the density output signal or signals and optionally the density ($\rho$) of the substance is calculated in accordance with the algorithm $$\rho = b_0 + b_1 C1 + b_2 (C2/C3) \quad (5)$$

where $b_0$, $b_1$ and $b_2$ are constants and C1, C2 and C3 are the measured Compton scatter count rates for preselected gamma-ray energies or energy ranges.

In a fourth embodiment this invention provides a method of producing a signal or signals related to the moisture content of a substance and from which the moisture content of the substance can be determined, the method comprising:
(a) locating at least two electrodes remote from the substance;
(b) generating an a.c. field between the electrodes whereby the field passes through the substance;
(c) measuring an a.c. sample signal resulting from the interaction of the field with the substance;
(d) measuring a.c. impedance, radio frequency loss or dielectric loss of the substance;
(e) deriving a moisture output signal or signals from the impedance, radio frequency loss or dielectric loss related to the moisture content of the substance.

In a preferred form of the fourth embodiment the method includes displaying the moisture output signal or signals.

In a particularly preferred form of the fourth embodiment the method also includes calculating the moisture content of the substance from the moisture output signal or signals and optionally the moisture content of the substance is calculated in accordance with the algorithm of eqn. (1).

In a fifth embodiment this invention provides a method of producing output signals related to the moisture content and density and/or thickness of a substance from which the moisture content, density and/or thickness of the substance can be determined, the method comprising the method of the fourth embodiment and:

(f) locating a gamma-ray source and a detector remote from the substance;

(g) irradiating the substance with gamma-rays from the source;

(h) measuring the intensities of gamma-rays backscattered from the substance with the detector;

(i) deriving a density and/or thickness output signal or signals from the measured intensities.

In a preferred form of the fifth embodiment the method includes displaying the density and/or thickness output signal or signals.

In a particularly preferred form of the fifth embodiment the method also includes calculating the moisture content, density and/or thickness of the substance from the moisture output and the density output signal or signals and optionally the moisture content of said substance is calculated in accordance with the algorithm of eqn. (2).

Alternatively the density ($\rho$) of the substance is calculated in accordance with the algorithm of eqn. (3) and the moisture content of the substance is calculated in accordance with the algorithm of eqn. (4).

In a sixth embodiment this invention provides a method of producing a signal or signals related to the density and/or thickness of a substance and from which the density and/or thickness of the substance can be determined, the method comprising:

(a) locating a gamma-ray source and a detector remote from the substance;

(b) irradiating the substance with gamma-rays from the source;

(c) measuring the intensities of gamma-rays backscattered from the substance with the detector;

(d) deriving a density and/or thickness output signal or signals from the measured intensities.

In a preferred form of the sixth embodiment the method includes displaying the density and/or thickness output signal or signals from the measured intensities.

In a particularly preferred form of the sixth embodiment the method also includes calculating the density and/or thickness of the substance the said density and/or thickness output signal or signals and optionally the density content of said substance is calculated in accordance with the algorithm of eqn. (5).

The invention finds particular application in the measurement of the moisture content, density and/or thickness of coal.

The electrodes are preferably on the same side of the substance. The gamma-ray source and detector are on the same side of the substance as each other but not necessarily on the same side as the electrodes. The conveyor belt can be rubber/canvas composite, canvas or rubber. The electrodes are preferably at least partially shielded from external electromagnetic interference by grounded means. Alternatively, the electrodes can be at least partially shielded by ungrounded insulating means.

When the electrodes are on the same side of the substance it is preferred that each electrode is at least partially shielded from the other electrode by grounded means to prevent the direct passage of the as electric field between the electrodes.

Where the electrodes are on the same side of the substance each electrode may be at least partially shielded from the other electrode by ungrounded insulating means to prevent the direct passage of the electric field between the electrodes.

Preferably the gamma-ray source and detector are at least partially shielded from each other by shielding means to prevent the direct passage of gamma-rays from the source to the detector. Preferably the shielding means is lead.

Preferably a backscattering substance volume from which gamma-rays are scattered and detected by the backscatter gauge is preselected to be about equal to an a.c. substance volume through which the a.c. electric field generated between the two electrodes passes.

The backscattering substance volume can be preselected by varying the energy of the gamma-ray source, gamma-ray source to substance distance, gamma-ray source to detector distance and/or the dimensions of the detector means.

The a.c. substance volume can be preselected by varying the areas of the electrodes, the intensity of the a.c. electric field therebetween, the electrode to substance distances and distance between electrodes.

Preferably the intensities of backscattered gamma-rays are measured in a selected energy range. It is preferred that the selected energy range includes an intensity peak of backscattered gamma-rays.

In another preferment the intensities of backscattered gamma-rays are measured in three selected energy ranges. Preferably one of the selected energy ranges includes an intensity peak of backscattered gamma-rays and each other selected energy range is selected to include part of a side of the energy peak for measuring the energy of the apex of the peak. The two other selected energy ranges are selected on opposite sides of the peak to each other.

A second gamma-ray source can be placed near the gamma-ray backscatter gauge for use in gain stabilisation.

The invention can also be used to determine the moisture content and/or density of a substance, in particular, coal, on a conveyor belt which is moving past the electrodes, and/or gamma-ray source and detector.

For the preferred forms of the invention wherein the backscattering substance volume is preselected to substantially equate with the a.c. substance volume and the intensities of backscattered gamma-rays are measured in three selected energy ranges where one of the preselected energy ranges includes an intensity peak of backscattered gamma-rays and each other selected energy range includes part of one of the sides of the energy peak to provide a measure of the energy of the apex of the peak, it has been advantageously found that the density and moisture content of coal can be determined.

Preferred embodiments of the invention are illustrated by way of example in the accompanying drawings in which.

Figure 1:
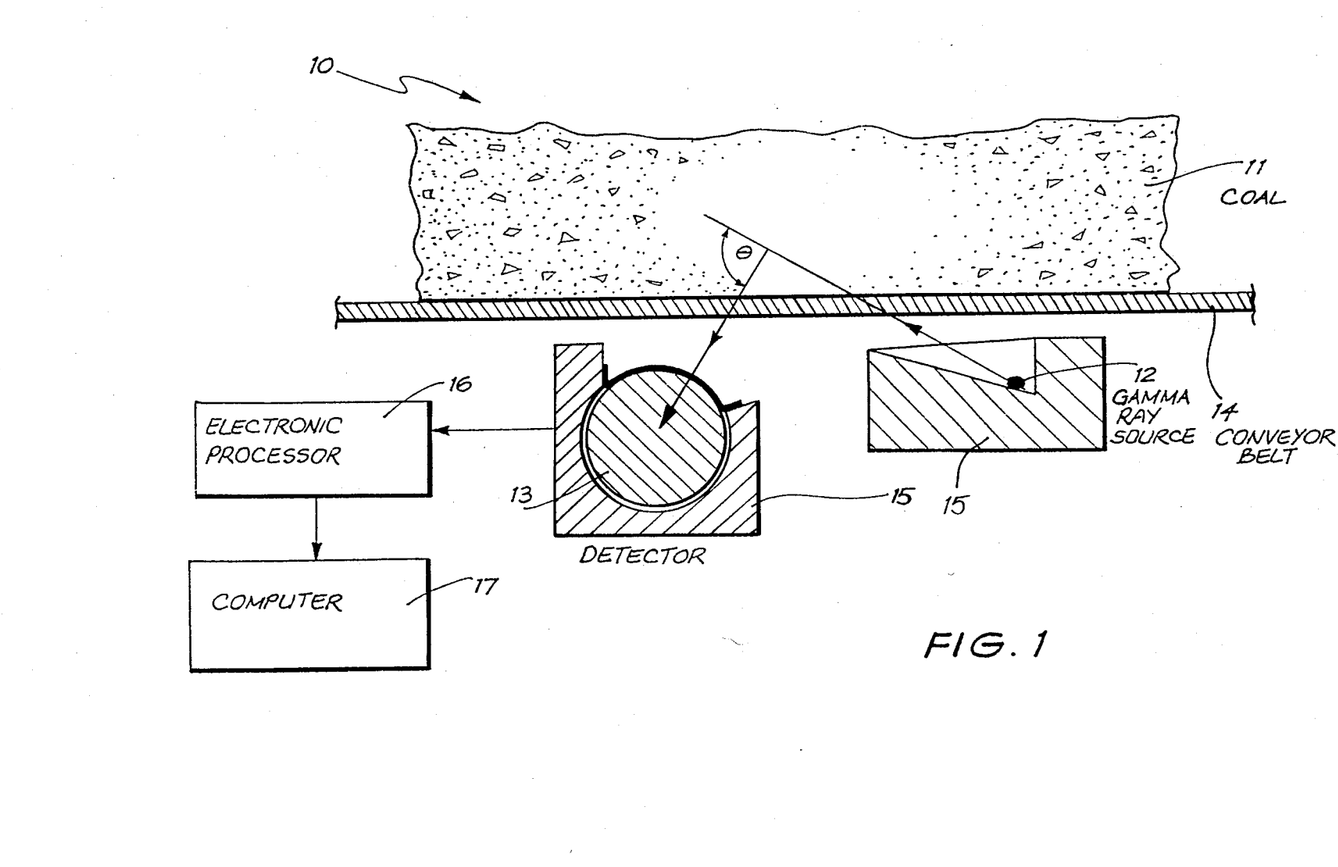
FIG. 1 is a schematic drawing of an apparatus to determine the density and/or thickness of coal by measuring the intensities of gamma-rays backscattered therefrom and calculating the coal density and/or thickness from the measured gamma-ray intensity values.

Referring to FIG. 1 an apparatus 10 for determining the density of coal 11 includes a $^{133}$Ba gamma-ray source 12 ($1.85 \times 10^7$ Bq) and a sodium iodide (thallium activated) detector 13 are remotely located from the coal underneath rubber conveyor belt 14. Gamma-ray source 12 and detector 13 are shielded from each other by lead shields 15 to prevent the direct passage of gamma-rays from source 12 to detector 13. The location of source 12 relative to detector 13 is such that gamma-rays from source 12 irradiate coal 11 and are subsequently backscattered by coal 11 and measured by detector 13 in three selected energy ranges. One of the selected energy ranges includes an intensity peak of backscattered gamma-rays and each other selected energy range includes part of a side of the energy peak for measuring the energy of the apex of the peak. The two other selected energy ranges are selected on opposite side of the peak. Electronic processor 16 which is linked to detector 13 derives a processor output signal or signals from the intensities measured by detector 13 which are related to the density of coal 11. Computer 17 which is connected to the output of processor 16 calculates the density of coal 11 from the processor output signal.

Figure 2:
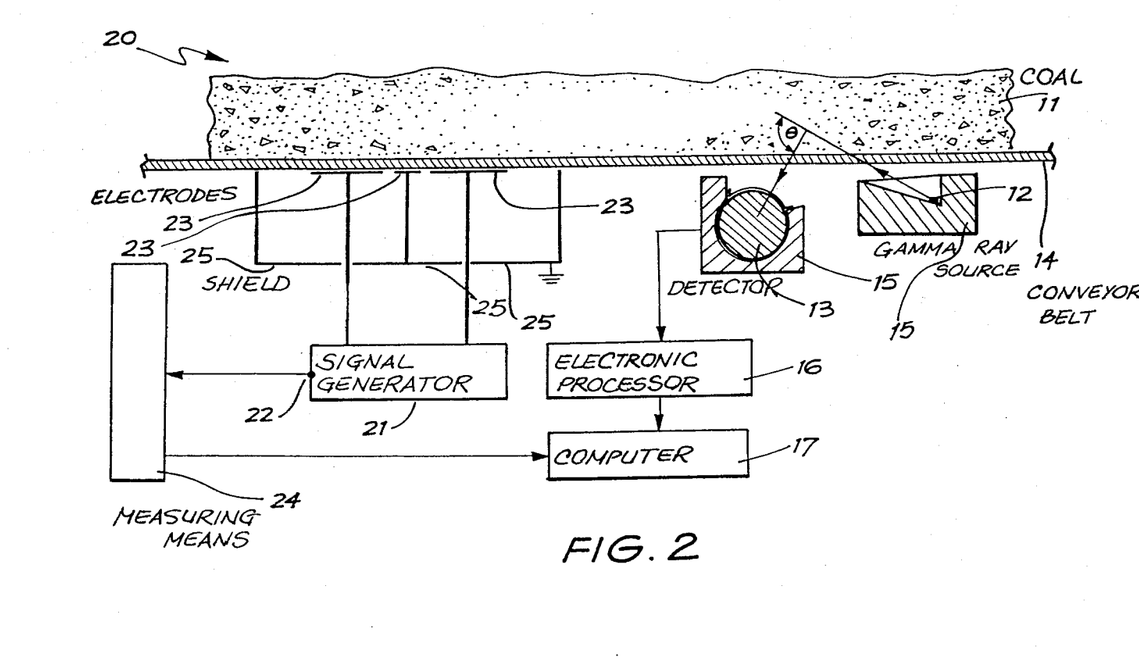
FIG. 2 is a schematic drawing of an apparatus to determine the moisture content, density and/or thickness of coal by measuring the a.c. impedance of coal and by measuring the intensities of gamma-rays backscattered therefrom and calculating the moisture content from the results obtained therefrom.

Referring to FIG. 2 an apparatus 20 for determining the moisture content of coal 11 includes a.c. signal generator 21 connected to measuring means 24 via output 22 which provides an a.c. reference signal to measuring means 24. Generator 21 is connected across two electrodes 23 located under a rubber conveyor belt 14 which transports coal 11.

Electrodes 23 are partially shielded from external electromagnetic interference by grounded metal shield 25. Metal shield 25 includes a central shield which at least partially shields electrodes 23 from each other to prevent the direct passage of the electric field from one electrode to the other electrode.

Electrodes 23 are located underneath conveyor belt 14 so that the a.c. field passes through coal 11.

Apparatus 20 also includes apparatus 10 of FIG. 1.

In apparatus 20 the volume of coal 11 interrogated by gamma-ray source 12 and detector 13 is chosen to equate with the volume of coal 11 interrogated by the a.c. field from electrodes 23.

The coal substance volume interrogated by gamma-rays can be preselected by varying the gamma-ray source 12 to coal 11 distance, gamma-ray source 12 to detector 13 distance, energy of gamma-rays by selecting the type of source 12 and/or the dimensions of detector 13.

The coal volume interrogated by the a.c. field from electrodes 23 can be preselected by varying the areas of electrodes 23, the intensity of the a.c. electric field therebetween, the electrode 23 to coal 11 distances and/or the distance between electrodes 23.

The intensities of backscattered gamma-rays are measured in three selected energy ranges. One of the selected energy ranges includes an intensity peak of backscattered gamma-rays and each other selected energy range includes part of side of the energy peak for measuring the energy of the apex of the peak. The two other selected energy ranges are selected on opposite sides of the peak to each other.

Computer 17 is associated with the output of measuring means 24 and electronic processor 16 and is used for calculating the susceptance, conductance and density of coal 11 from the measurements obtained therefrom and the moisture content of coal 11 is then calculated from the calculated values of the susceptance, conductance and density.

EXAMPLE 1

Samples of total product coal (−3+0 mm) were prepared to an accurately known moisture content and packed in sealed plastic containers (of dimension, 260×185×80 mm) such that the sample thickness was either 50 or 75 mm.

Referring to FIG. 2 coal 11 was placed directly above under-belt electrodes 23, and separated from them by 8.5 mm thick conveyor belt 14.

The (parallel) susceptance (C) and conductance (G) components of the measured a.c. impedance were correlated with oven dried moisture.

The results for two samples are summarised in Table 1.

TABLE 1

CORRESPONDENCE BETWEEN "CAPACITANCE MOISTURE" AND OVEN DRIED MOISTURE FOR THE CAPACITANCE SENSOR OF FIG. 2

| Sample Description | | Correlation with oven dried moisture | |
|---|---|---|---|
| Identification # | Thickness (cm) | Moisture (wt %) | rsm error (wt % H$_2$O) |
| BHP | 5.0 | 0–15 | 0.39 |
| UDC | 5.0 | 0–19 | 0.31 |
|  | 7.5 | 0–19 | 0.26 |

Total product coal (−3 + 0 mm) from Utah Development Company (UDC) and Broken Hill Proprietary Company Ltd. (BHP) washeries
*C - susceptance, G - conductance In each case the oven dried moisture content was correlated with measured parameters (C,G) using an equation of the form of eqn. (1).

When the sample thickness (50 or 75 mm) is constant, and over a restricted range of moisture, susceptance (C) and conductance (G) are required in the correlation (with oven dried moisture) to obtain an rms error that is typically 0.4 wt% H$_2$O.

EXAMPLE 2

In a gamma-ray backscatter assembly the single scattering output, P, can be expressed as follows:

$$p\alpha \sum_X \sum_Y \sum_Z NP_1 P_2 P_3 \tag{6}$$

wherein
X, Y, Z=Cartesian co-ordinates
N=number of electrons in volume element $\Delta v$,
P$_1$=probability that gamma-ray will reach $\Delta v$, $P_2$ = probability that gamma-ray scattered in direction of detector, $P_3$ = probability that scattered gamma-ray reaches the detector.

The terms $P_1$, and $P_3$ are of the form $1/R^2 \exp(-\mu x)$ where R is the distance from the source (or detector) to $\Delta v$, $\mu$ the gamma-ray absorption coefficient and x the distance the gamma-ray must travel through the sample. The geometry dependent term in the assembly response is therefore approximately proportional to $P_1 \cdot P_3$ which is equal to $(1/R_i^2 R_o^2)$, $\exp(-\mu_i x_i - \mu_o x_o)$ where the subscripts i and o refer to the incoming and outgoing radiations, respectively.

For constant source to detector distance and increased source to sample distances, the relative effect of the $(1/R_i^2 R_o^2)$ term is reduced and sample penetration is effectively increased.

Figure 4:
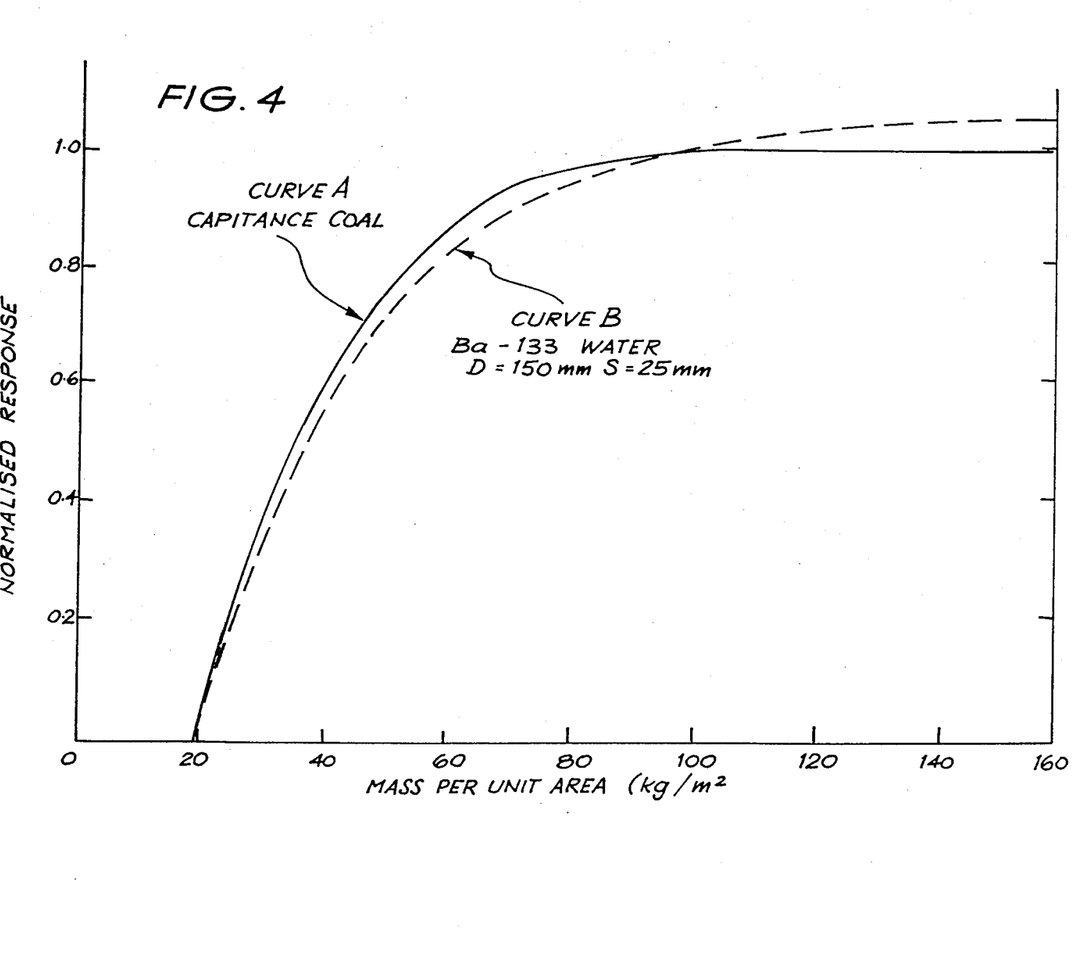
FIG. 4 shows the experimental relative values of parallel susceptance (C) and intensity of backscattered gamma-rays as a function of sample thickness for a coal sample using the apparatus of FIG. 2.

Curve A in FIG. 4 shows the experimental relative values of parallel susceptance (C) as a function of sample thickness for a coal sample on the apparatus 20 (FIG. 2). The gamma-ray detector 13 was chosen so depth response of backscatter count rate matched that of the electric field between electrodes 23. Parameters which were optimised to achieve good matching include the energy of source gamma-rays, source to sample distance, gamma-ray source to detector distance and detector size. The depth response of the gamma-ray backscatter count rate is shown as Curve B in FIG. 4.

Figure 3:
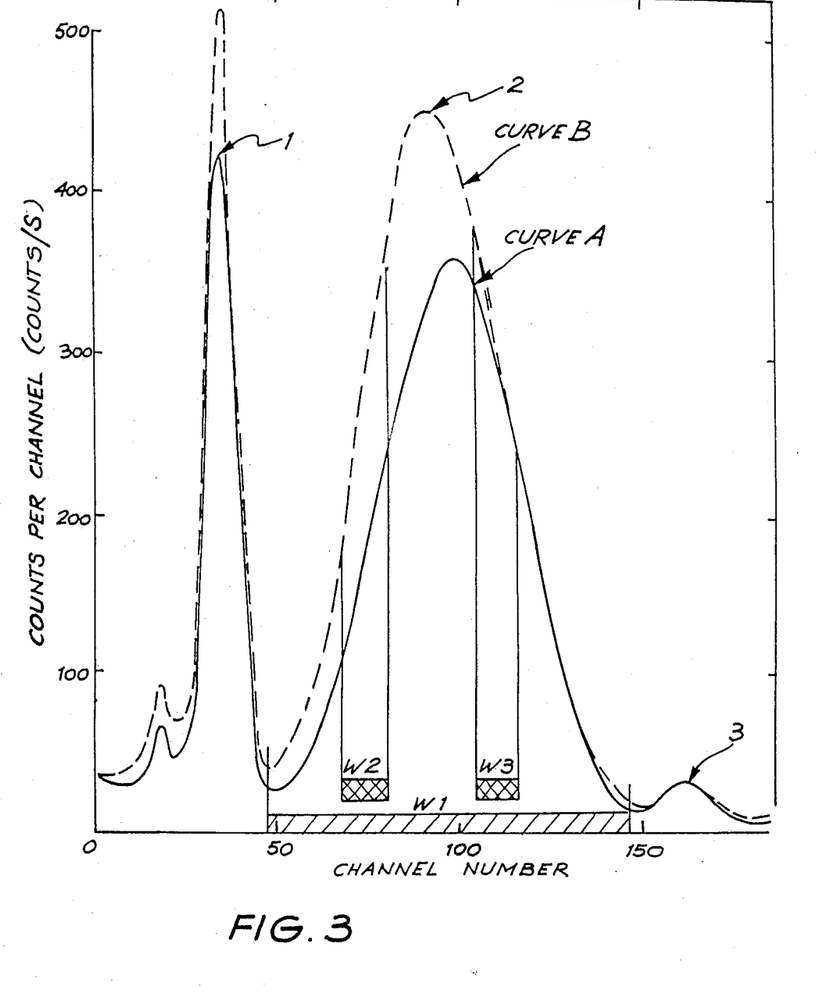
FIG. 3 is a typical pulse height versus channel spectrum obtained from coal using the apparatus of FIG. 1.

The measured count rate of Compton scattered gamma-rays in FIG. 3 gives an acceptable measure of density for coal sample thicknesses greater than about 120 mm. Therefore, the samples thicker than about 120 mm, an equation of the form of eqn. (2) can be used for moisture determination with C and G determined from the measured a.c. impedance and density ($\rho$) measured on a matched gamma-ray backscatter gauge. However, for samples of thickness less than 120 mm, Compton backscatter count rate does not give an acceptable measure of density as it depends on density and thickness and therefore a different approach is required.

EXAMPLE 3

A preferred method of correcting under-belt a.c. impedance measurements for changes in density of substance on conveyor belts is described. The present method allows density compensation over a wide range of thicknesses including those less than about 120 mm (at densities ~0..8—1.2 g.cm$^3$).

The method uses a matched gamma-ray/a.c. electric field substance volume similar to that described in Example 2 and shown in FIG. 4.

Typical pulse height spectra measured with this gauge are shown in FIG. 3. Curves A and B represent spectra measured with samples of thickness 20 mm and 60 mm, respectively. Peak 1 represents lead K X-rays (75 keV), peak 2 represents Compton scattered gamma-rays and peak 3 represents gamma-rays from a second $^{133}$Ba source placed near the detector (365 keV). Peak 3 is used for gain stabilisation.

The energy of Compton scatter gamma-rays (E') depends on the angle $\Theta$ (ref. FIG. 2) through which the gamma-rays are scattered. $E^1$ is calculated using the equation $$E^1 = E_0 / \left( 1 + \frac{E_0}{0.511} (1 - \cos\theta) \right) \quad (7)$$

where $E_0$ is the incident gamma-ray energy in MeV. The energy of the Compton scatter peak in FIG. 3 can therefore be used to indicate the sample thickness as the average scattering angle is increased for thicker samples. By combining a measure of Compton scatter count rate (using window W1 in FIG. 3) with a parameter which gives a measure of peak position (such as the ratio of count rates in windows W2 and W3), apparatus in FIG. 2 can be used to measure density independent of thickness using an equation of the form of eqn. (5) where C1, C2, and C3 are measured count rates in windows W1, W2 and W3, respectively. The third term in Equation (5) can be any parameter which gives a measure of peak position e.g. peak position at maximum channel count rate, peak fitting etc.

Moisture may then be determined from the results of the a.c. impedance and gamma-ray backscatter measurements by combining equations (2) and (3) into a single equation of the form of eqn. (4).

The accuracy of density determination using apparatus 20 in FIG. 2 was tested using samples of kerosene (density 0.792 g.cm$^{-3}$), water (density 1.00 g.cm$^{-2}$) and citric acid (density 1.168 g.cm$^{-2}$), each of thickness 20 to 200 mm in 20 mm steps. The results show that density can be determined using equation (5) to within 0.03 g.cm$^{-3}$ over this range of thickness and density. For the thickness range 40 to 200 mm this root-mean-square error drops to 0.022 g.cm$^{-3}$.

Samples of coal were prepared to an accurately known moisture content and packed in sealed plastic containers (of dimensions 260×185×80 mm) such that the sample thickness was in the range 25 to 65 mm. Referring to FIG. 2, coal 11 was placed directly above the under-belt electrodes 23 and directly above the source 12 and detector 13 (FIG. 2), on top of an 8.5 mm thick conveyor belt 14.

Moisture determined with and without the gamma-ray backscatter gauge using eqns. (4) and (2), respectively, were correlated with oven-dried moisture. Density in eqn. (2) was determined from sample thickness and mass.

The results of these measurements are summarised in Table 2. The combined a.c. impedance and gamma-ray backscatter measurements are significantly more accurate than the combined a.c. impedance and physical density measurements. As well, the gamma-ray backscatter apparatus is better suited to on-line measurement than physical density measurement techniques.

TABLE 2

| Sample Description | | Root-mean-square error (wt % moisture) | |
|---|---|---|---|
| Indentification* | Thickness (mm) | Moisture (wt %) | Equation (2) | Equation (4) |
| UDC - Blackwater | 40–65 | 13–27 | 1.16 | 0.21 |
| BHP - Newcastle | 50–65 | 0–15 | 0.63 | 0.31 |
| BHP - Metropolitan | 50–65 | 0–15 | 0.78 | 0.45 |
| BHP - Newcastle | 25–65 | 0–15 | 0.73 | 0.51 |
| BHP - | 25–65 | 0–15 | 1.01 | 0.69 |

TABLE 2-continued

| Sample Description | | Root-mean-square error (wt % moisture) | |
|---|---|---|---|
| Indentification* | Thickness (mm) | Moisture (wt %) | Equation (2) | Equation (4) |
| Metropolitan | | | | |

*BHP samples are total coking coal product (−3 + 0 mm) from Broken Hill Proprietary Company Ltd. UDC samples are filter cake product (−0.5 + 0 mm) from Utah Development Company.

What we claim is:

1. An apparatus for producing signals related to the moisture content and density of a substance from which the moisture content of said substance can be determined, said apparatus comprising:
   (a) two electrodes;
   (b) an a.c. signal generator connected across said two electrodes, said electrodes being located remote from the substance whereby an ac field generated therebetween passes through said substance; and
   (c) measuring means operatively associated with or coupled to said generator and said electrodes so as to receive an a.c. sample signal related to said field passing through said substance wherein said measuring means is adapted to measure a.c. impedance, radio frequency loss or dielectric loss of said substance and to derive a moisture output signal therefrom related to the moisture content of said substance;
   in combination with:
   (d) a gamma-ray source and a detector which are located in close proximity to said substance wherein gamma-rays from said source irradiate said substance and the intensities of backscattered gamma-rays are measured by said detector; and
   (e) processing means operatively associated with or coupled to said detector for deriving a density/thickness output signal from the measured intensities which is related to the density/thickness of said substance; and
   (f) calculating means associated with said measuring means and processing means for calculating the moisture content of said substance from said moisture and said density/thickness output signals; and
   wherein the substance volume through which said field passes is selected to be about equal to the substance volume from which backscattered gamma-rays are detected by said detector.

2. An apparatus according to claim 1 wherein said two electrodes are plate electrodes which are located on the same side of the substance with the major areas of the electrodes directed towards said substance and wherein said electrodes are electrically shielded from each other to substantially prevent the direct passage of said field between said electrodes.

3. An apparatus according to claim 2 wherein said electrodes are electrically shielded from each other to substantially prevent the direct passage of said field between said electrodes by a grounded electrical conductor.

4. An apparatus according to claim 1 wherein the moisture content of said substance is calculated in accordance with the algorithm $$\text{Moisture} = a_0 + a_1 C + a_2 G + a_3 \rho$$

where $a_0$, $a_1$, $a_2$ and $a_3$ are constants, C is susceptance, G is conductance of said substance and $\rho$ is density of said substance.

5. An apparatus according to claim 4 wherein the density ($\rho$) of said substance is calculated in accordance with the algorithm $$\rho = b_0 + b_1 c_1 + b_2 (C_2/C_3)$$

wherein $b_0$, $b_1$ and $b_2$ are constants and C1, C2 and C3 are the measured Compton scatter count rates for preselected gamma-ray energies or energy ranges.

6. An apparatus according to claim 1 wherein said source and said detector are on the same side of said substance and said electrodes are on the same side of said substance as said source and said detector.

7. An apparatus according to claim 1 wherein said source and said detector are shielded from each other to prevent direct passage of gamma-rays from said source to said detector.

8. A method of producing signals related to the moisture content and density of a substance from which the moisture content of said substance can be determined, said method comprising:
   (a) locating two electrodes in the near vicinity of the substance whereby an a.c. field generated therebetween passes through the substance;
   (b) generating an a.c. field between said electrodes whereby said field passes through said substance;
   (c) measuring an a.c. sample signal resulting from the interaction of field with said substance;
   (d) measuring a.c. impedance, radio frequency loss or dielectric loss of said substance;
   (e) deriving a moisture output signal from said impedance, radio frequency loss or dielectric loss related to the moisture content of said substance;
   in combination with:
   (f) locating a gamma-ray source and a detector in close proximity to said substance;
   (g) irradiating said substance with gamma-rays from said source;
   (h) measuring the intensities of gamma-rays backscattered from said substance with said detector;
   (i) deriving a density/thickness output signal from said measured intensities;
   (j) determining the moisture content of said substance from said moisture output signal and said density/thickness output signal; and
   wherein the substance volume through which said field passes is selected to substantially equate with the substance volume from which backscattered gamma-rays are detected.

9. A method according to claim 8 wherein said two electrodes are plate electrodes which are located on the same side of the substance with the major areas of the electrodes directed towards said substance and wherein said method further comprises electrically shielding said electrodes from each other to substantially prevent the direct passage of said field between said electrodes.

10. A method according to claim 8 wherein the moisture content of said substance is determined in accordance with the algorithm $$\text{Moisture} = a_0 + a_1 C + a_2 G + a_3 \rho$$

where $a_0$, $a_1$, $a_2$ and $a_3$ are constants, C is susceptance, G is conductance of said substance and $\rho$ is density of said substance.

11. A method according to claim 10 wherein the density ($\rho$) of said substance is calculated in accordance with the algorithm $$\rho = b_0 + b_1 C1 + b_2(C2/C3)$$

where $b_0$, $b_1$ and $b_2$ are constants and C1, C2 and C3 are the measured Compton scatter count rates for preselected gamma-ray energies or energy ranges.

12. A method according to claim 8 wherein said source and said detector are located on the same side of said substance.

13. A method according to claim 8 wherein said electrodes are located on the same side of the substance as said source and said detector.

14. A method according to claim 8 wherein said substance is coal.

15. A method according to claim 8 wherein said electrodes are at least partially shielded from external electromagnetic interference.

* * * * *